United States Patent [19]

McCabe et al.

[11] Patent Number: 5,780,100
[45] Date of Patent: Jul. 14, 1998

[54] METHOD AND APPARATUS FOR PREPARING SAMPLE CARTRIDGES FOR PARTICLE ACCELERATION DEVICE

[75] Inventors: Dennis E. McCabe, Middleton; Richard J. Heinzen, North Freedom, both of Wis.

[73] Assignee: PowderJect Vaccines, Inc., Madison, Wis.

[21] Appl. No.: 444,173

[22] Filed: May 18, 1995

[51] Int. Cl.[6] .............................. B05D 7/22; B05D 3/12; B05D 3/04; C12N 15/00
[52] U.S. Cl. .................... 427/183; 427/2.11; 427/231; 427/232; 427/240; 427/346; 427/378
[58] Field of Search ........................ 427/2.1, 2.11, 427/232, 4, 2.14, 240, 238, 237, 346, 231, 183, 378

[56] References Cited

U.S. PATENT DOCUMENTS

| | | | |
|---|---|---|---|
| 2,066,592 | 1/1937 | Wadsworth | 427/232 |
| 2,682,872 | 7/1954 | Bower | 427/231 |
| 4,088,802 | 5/1978 | Shriver, Jr. | 427/232 |
| 4,337,104 | 6/1982 | Lynn | 427/2.1 |
| 4,347,204 | 8/1982 | Takagi et al. | 427/2.11 |
| 4,418,691 | 12/1983 | Yannas et al. | 128/156 |
| 4,634,447 | 1/1987 | Isono et al. | 427/235 |
| 4,659,584 | 4/1987 | Schilk | 427/2.1 |
| 4,756,922 | 7/1988 | Motoyama et al. | 427/4 |
| 4,945,050 | 7/1990 | Sanford et al. | 435/172.8 |
| 5,015,580 | 5/1991 | Christou et al. | 435/172.3 |
| 5,120,657 | 6/1992 | McCabe et al. | 435/287 |
| 5,149,655 | 9/1992 | McCabe et al. | 435/287 |
| 5,204,253 | 4/1993 | Sanford et al. | 435/172.3 |
| 5,405,779 | 4/1995 | McCabe et al. | 435/287 |
| 5,456,940 | 10/1995 | Funderburk | 427/2.1 |
| 5,637,477 | 6/1997 | Spaulding et al. | 435/69.1 |

FOREIGN PATENT DOCUMENTS

0301749A2   5/1988   European Pat. Off. .

OTHER PUBLICATIONS

Klein, T.M., et al., "Particle Gun Technology: A Novel Method for the Introduction of DNA into Living Cells," Abstract for Post 28 in *Biotechnology in Plant Science: Relevance to Agriculture in the Eighties*, International Symposium, Ithaca, NY (1985), Jun.

Klein, T.M., et al., "High Velocity Microprojectiles for Delivering Nucleic Acids into Living Cells," *Nature*, 327:70–73 (1987) May.

Klein, T.M., et al., "Stable Genetic Transformation of Intect Nicotiana Cells by the Particle Bombardment Process," *Proc. Natl. Acad. Sci. USA*, 85:8502–8505 (1988) Nov.

McCabe, D.E., et al., "Stable Transformation of Soybean (*Glycine max*) by Particle Acceleration," *Bio/Technology*, 6:923–926 (1988) Aug.

Sanford, J.C., "The Biolistic Process," *TIBTECH*, 6:299–302 (1988) no month.

Sanford, J.C., et al., "Delivery of Substances into Cells and Tissues Using a particle Bombardment Process," *Particulate Science and Techn.*, 5:27–38 (1987) no month.

*Primary Examiner*—Diana Dudash
*Attorney, Agent, or Firm*—Robins & Associates

[57]   ABSTRACT

A method for depositing particles coated with biological substances onto the concave inner surface of a length of tubing includes the steps of preparing a uniform suspension of coated particles, introducing the particles into the tubing, placing the tubing into a generally horizontal position, removing the evaporable liquid after the particles have settled, and drying the particles. When dry, the tubing is cut into sample cartridges of appropriate length for use in a particle acceleration instrument.

An apparatus for performing the method is also disclosed.

4 Claims, 3 Drawing Sheets

METHOD AND APPARATUS FOR PREPARING SAMPLE CARTRIDGES FOR PARTICLE ACCELERATION DEVICE

FIELD OF THE INVENTION

The present invention relates to the field of delivering particles coated with biological substances into cells and more particularly to a method and apparatus for preparing samples for delivery.

BACKGROUND OF THE INVENTION

In the past decade, particle-mediated acceleration of material, particularly genetic material, into living cells and tissues has emerged as an important tool of plant and animal biotechnology. Transient expression and germ line integration of introduced DNA has been demonstrated in microorganisms, plants, and animals.

As the fundamentals of the technology have been worked out, attention has increasingly shifted toward development of devices that offer the operator the ability to perform a series of particle-mediated gene transfers sequentially in rapid succession. Such a device would be particularly advantageous for use in mass immunization of humans or domesticated animals with genetic vaccines.

One limitation of existing particle-mediated gene transfer devices is the form in which the sample is provided. In all such devices, the sample is deposited upon the surface of small, dense particles of a material such as gold or platinum. The coated-particles are themselves then coated onto either a rigid surface, such as a metal plate, or onto a carrier sheet made of a fragile material such as mylar. The coated sheet is then accelerated toward a target. This approach has several advantages as well as some disadvantages. The advantages have to do with the fact that the planar sheet generates a very uniform spread of accelerated particles. One disadvantage is that, each particle-coated plate or carrier sheet is prepared individually and may be used only once, making particle acceleration a time-consuming and inefficient process, particularly when many repetitive gene transfers are envisioned. Each coated carrier sheet is relatively large and must be handled with care, to avoid damage or contamination. It is also sometimes difficult to distinguish the useful coated side of a carrier sheet from the uncoated side. Improper positioning of the carrier sheet can reduce throughput and can result in wasted samples.

The distribution or spread of the pattern of carrier particles may be more critical for some applications, i.e. when germ line events are desired, than for other applications, especially when only transient expression of the introduced genes is needed. When an infrequent germline transformation event is desired, it is necessary to uniformly accelerate particles toward a large area of cells or tissues. To date therefore, it has been considered desirable to distribute the coated-particles as a monolayer on a relatively large surface before accelerating them toward a target to maximize the number of cells receiving particles under precisely uniform conditions, and to thereby increase the likelihood that one cell will undergo a germline transformation. In contrast, when accelerating particles into cells to induce transient gene expression in somatic tissues such as skin, there is a less compelling need to make precisely uniform the acceleration of the particles, since adequate expression can take place even with low numbers of cells actually penetrated by particles. Therefore, particle delivery techniques that to date have been undesirable now become desirable.

To overcome these and other limitations, what is desired is a high throughput gene delivery apparatus that can accept a plurality of samples for rapid and sequential delivery into target tissues. What is also desired is a sample storage and delivery platform that is more durable, and easier to prepare, store, and handle than existing platforms.

SUMMARY OF THE INVENTION

The invention is summarized in that a method for depositing particles in a length of tubing comprises the steps of preparing in an evaporable liquid a uniformly dispersed suspension of particles, distributing the uniformly dispersed particle suspension on a concave inner surface of a length of tubing having first and second ends, removing most of the evaporable liquid, but not the settled particles, from the inner surface, and drying the distributed particles.

Before being deposited, the particles are coated at a suitable density with a biological substance for delivery into a target and are of sufficiently small size that they are small in relation to the size of the organism which they are intended to transform and sufficiently dense to readily retain momentum.

The present invention is further summarized in that an apparatus for depositing particles in a length of tubing comprises a mounting base, a tubing roller having an axis of rotation and a tubing bore passing through the axis of rotation, the tubing bore having first and second ends and being sized for removable insertion of the tubing therein, the tubing roller being rotatably secured to the mounting base so that the tubing bore is in a generally horizontal orientation, a rotator operably connected to the tubing roller, and gas delivery means connectable to a source of a drying gas.

It is an object of the present invention to provide a method and an apparatus for forming a large number of particle cartridges for use in a gas driven particle acceleration device.

It is an advantage of the present invention that a large number of substantially identical sample cartridges can be prepared in a single effort.

Other objects, advantages and features of the present invention will become apparent upon consideration of the following specification read in conjunction with the accompanying drawings.

DETAILED DESCRIPTION OF THE INVENTION

Figure 1:
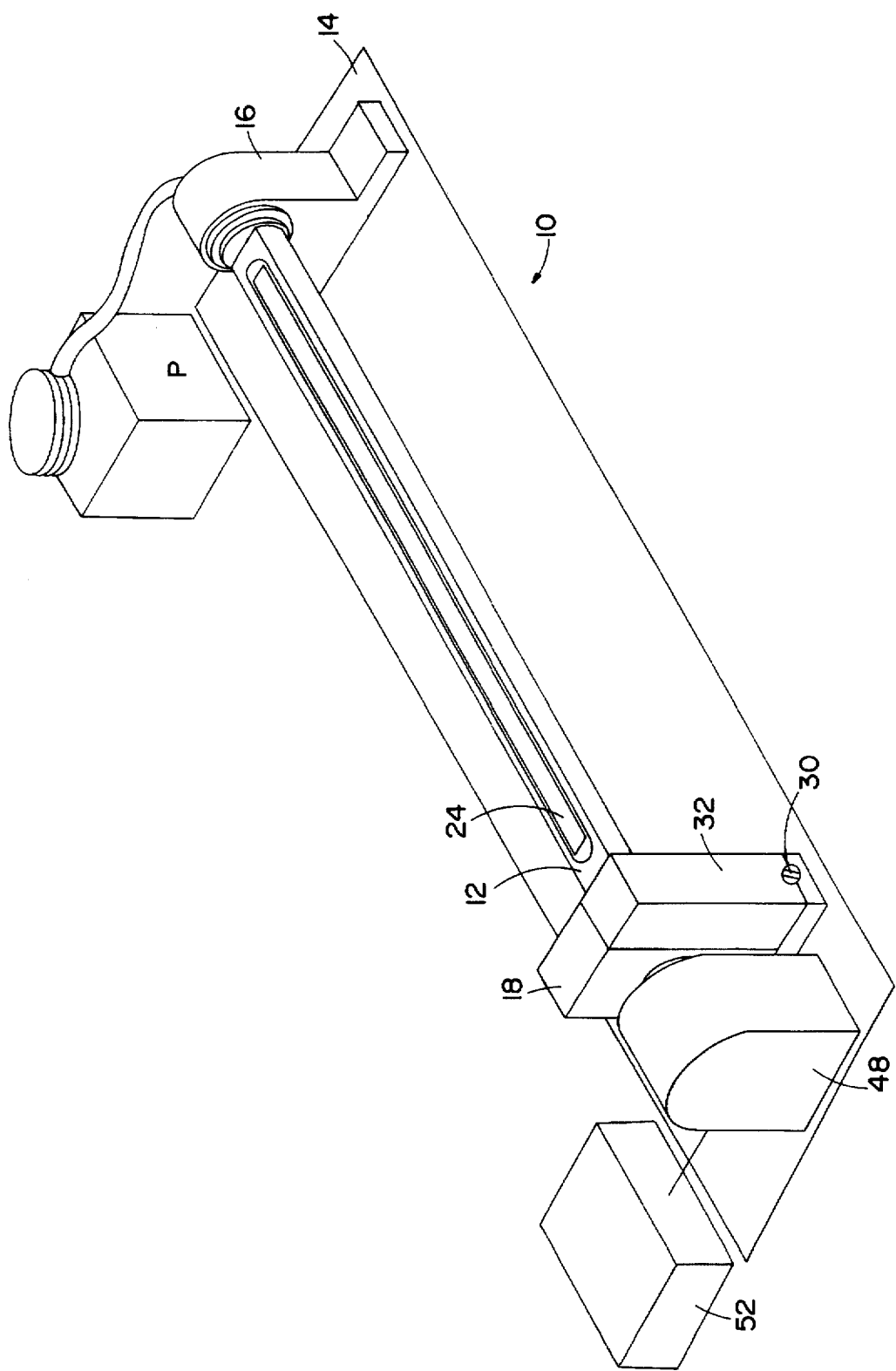
FIG. 1 is a view of a preferred embodiment of the present invention.
Figure 2:
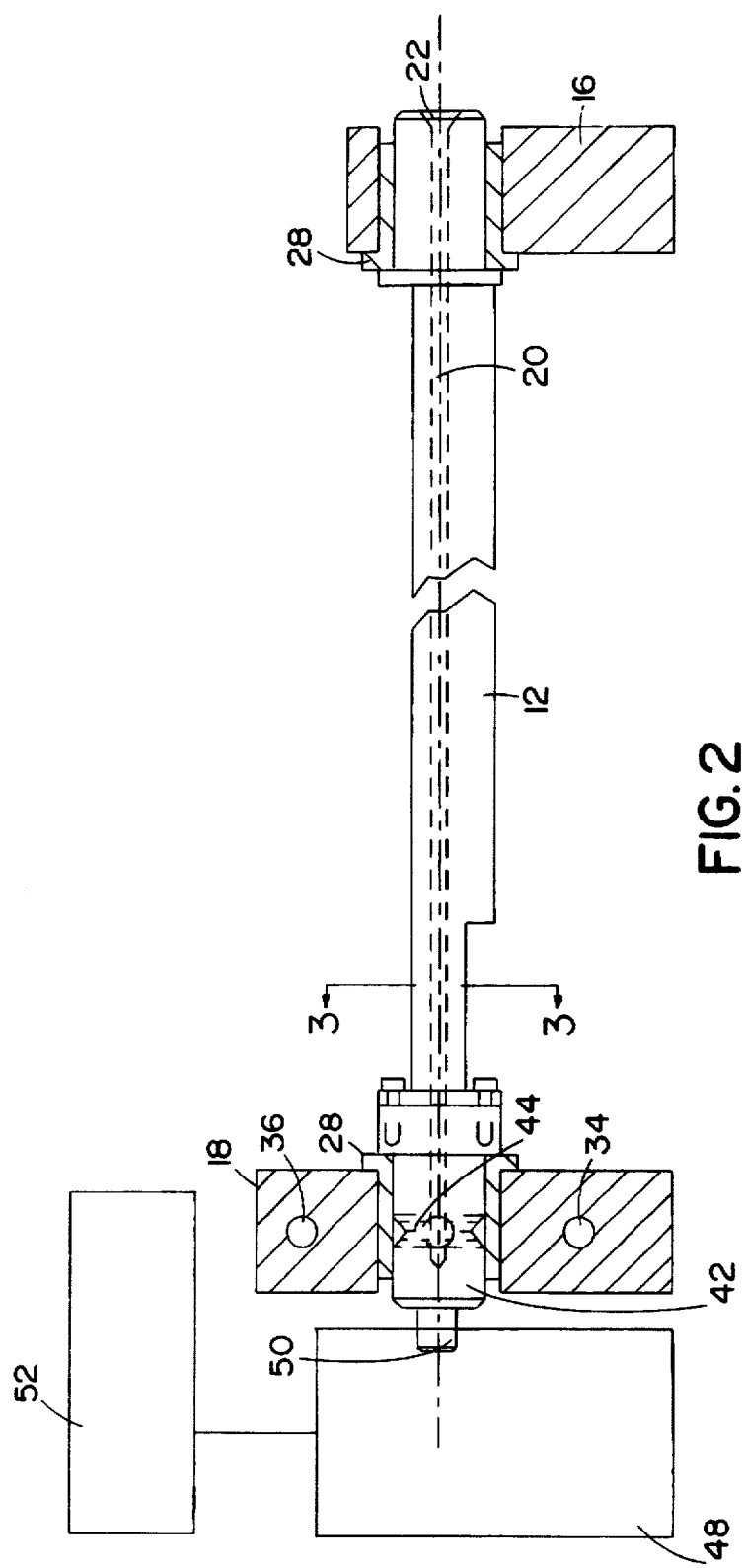
FIG. 2 is a cut away view of a portion of the apparatus of FIG. 1.
Figure 3:
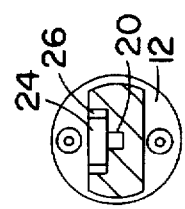
FIG. 3 is a cross-sectional view taken along line 3—3 of FIG. 1.
Figure 4:
FIG. 4 is a top view of a preferred embodiment of the tubing roller portion of the invention.
Figure 5:
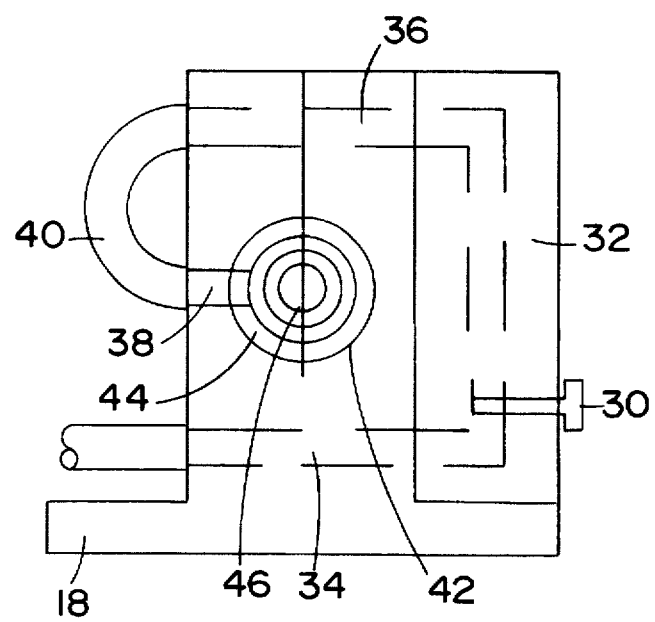
FIG. 5 is a cut away view of a preferred embodiment of the gas delivery means of the present invention.

The present invention provides a reproducible method for forming a large number of sample cartridges for use in a gas-driven particle acceleration instrument. Small dense particles are reversibly coated onto a concave inner surface of the sample cartridges. The particles are themselves reversibly coated with biological substances such as genetic material or protein. During particle acceleration and delivery, a gas stream passing over the deposited particles releases the particles from the sample cartridge and carries them into a target cell, tissue, or organism.

For repeatability during delivery, it is important that the number of particles delivered from each sample cartridge be ascertainable and relatively constant, at least within a statistically acceptable range such as ±20%, but preferably ±10%, of an experimentally determined mean number. It is also important that the particle distribution within the sample cartridges be substantially constant, to maximize sample-to-sample reproducibility from one cartridge to the next. These goals are achieved by the method of the present invention, described in detail below.

To prepare sample cartridges, suitable tubing having a concave inner surface is filled with a uniform suspension of the coated particles in an evaporable liquid as follows. The coated-particle suspension is vortexed and sonicated to achieve uniformity of the coated particles prior to placement into the tubing. An axial bore through the tubing provides a concave inner surface. It is preferred that the tubing be transparent or translucent so that the particles coated onto the inner concave surface of the tubing can be visually observed. All tubing used should be inert to reaction with the selected liquid-drying gas and should be sufficiently durable to retain mechanical stability throughout the gene delivery process. Tefzel® tubing (⅛" O.D.×3/32" I.D.) has been found to be suitable. This tubing has an internal capacity of about 0.8 ml/7" length. One end of the tubing is connected to an aspirator, such as a barrel syringe, using a liquidtight adapter. The opposite end of the tubing is placed into the coated-particle suspension. Using the aspirator, the suspension is drawn into the tubing until the tubing is full. Since it is preferred that there be no water in the tubing, in high humidity conditions it is suggested that a sufficient amount of 100% ethanol be drawn through the tubing to exclude residual water from the interior of the tube before the particles are drawn into the tube.

The filled tubing is then inserted into the axial bore of the apparatus (described below) and is thus held firmly in a generally horizontal orientation until the particles in the tubing settle out of suspension onto the concave inner surface of the tubing. Settling is substantially complete in about 3 minutes, but it may be possible to achieve settling in less time. When the particles have settled, most of the evaporable liquid is removed from the horizontal tubing bore, leaving the wet, settled particles attached to the concave inner surface of the tubing. The liquid is preferably removed at a slow, constant rate so as not to disturb the particles which are settled, but which are not yet reversibly attached to the tubing. While this can be performed manually with a very steady hand, the liquid is preferably removed using a liquid-withdrawing pump such as a peristaltic pump connected to one end of the tubing so as to withdraw liquid. A suitable liquid withdrawal rate that does not disturb the settled particles is 2–3 inches per second.

When most of the evaporable liquid has been withdrawn, the tubing can be rotated about a generally horizontal axis of rotation coaxial with the central tubing bore for a length of time sufficient to distribute the wet, settled particles around at least a portion of the concave inner surface of the tubing. A rotation rate of 10–30, preferably 20, revolutions per minute is suitable. At this rate, the settled particles are sufficiently distributed in about 30 seconds, although longer rotation times are also acceptable. Alternatively, it may be preferred to rotate the tube only 180° to drain liquid away from the beads before drying.

Finally, the settled particles are dried by removing the residual evaporable liquid from the tubing. This is readily achieved by introducing a liquid-drying gas, such as air or nitrogen gas, into one end of the tubing at a flow rate of approximately 350–400 milliliters per minute for 3–5 minutes or until the settled particles are completely dry. If desired the particles can also be air-dried under ambient, low-humidity conditions, though drying time will be longer. When the particles are dry, the distribution of particles in the tubing is tested, as described herein, and if found to be acceptably evenly distributed, individual sample cartridges are formed by cutting the tubing into pieces of a predetermined length, generally ½".

Methods for coating the small, dense particles with a biological substance for use in the described method are known. Any such method can be used to prepare the coated particles. A preferred method for coating DNA onto gold particles for use in the particle-depositing method of the present invention follows below. One of ordinary skill will appreciate from the following description the importance of determining with an acceptable tolerance the amount of biological substance per particle and the number of particles per sample cartridge. The acceptable tolerance levels should be about ±30%, preferably about ±20% and most preferably about ±10% of the desired amount.

Gold particles are preferred for coating. Most preferred are 0.95 micron amorphous gold or 1–3 micron gold beads. In this patent application, references to "beads" or "particles" are intended to include, without limitation, both spherical and amorphous particles of appropriate size and density. DNA is a preferred biological substance for coating onto particles. However, other substances including, but not limited to, RNA and proteinaceous materials can also be coated onto particles. Subsequent description and examples refer to the use of gold particles coated with DNA, although the invention is not intended to be so limited. Conditions for depositing other biological substances or for using non-gold particles can vary from the method stated in ways that are understood in the art.

A desired amount of the gold particles is placed in a centrifuge tube. The amount of gold used can be roughly determined by multiplying the desired number of particles per delivery by the number of sample cartridges being prepared. A suitable amount of particles per delivery is typically on the order of 0.25–0.5 milligrams gold per delivery, although acceptable amounts can be higher or lower. By routine experimentation, one can ascertain limits on particle delivery amounts below which the transfer is acceptably high (by any ascertainable measure, such as gene expression level or biological response to treatment) while the trauma to target tissues is minimal. Minimal trauma in an animal target tissue is evidenced by only a slight reddening of the target area.

A small volume (100–300 μl) of 0.1M spermidine is added to the tube and a suspension of single coated particles is formed by sonicating the contents of the tube for a sufficient length of time, generally for a few seconds.

An appropriate volume of DNA, suspended in a buffer that does not affect its integrity or stability, is added to the particle/spermidine suspension to achieve an acceptable DNA loading rate. The DNA, spermidine, and gold particles are mixed by vortexing. The DNA loading rate is the average density of DNA per particle, expressed for a bulk population (e.g., μg of DNA per mg of particles). Preferred effective DNA loading rates on gold particles range from 0.1 to 5.0 micrograms of DNA per milligram of gold. Exceeding 10.0 micrograms of DNA per milligram of gold is not preferred as it can lead to clumping of gold particles. However, as little as 0.001 micrograms of DNA per milligram of gold is adequate to achieve significant expression from some expression vectors.

It is noted that, to obtain the most uniform coating results, the volume of DNA should not exceed the volume of spermidine, but smaller volumes may be used. Accordingly, it may be necessary to adjust either the concentration of plasmid DNA or the volume of spermidine added initially to the gold particles.

Calcium chloride ($CaCl_2$) is then added to the mixture while gently vortexing. A sufficient amount of calcium chloride is added to result in precipitation of DNA-coated gold particles. If 2.5M calcium chloride is added, a suitable volume is equal to the volume of spermidine added earlier. The mixture is allowed to precipitate at room temperature for at least 5 or 10 minutes. At DNA loading rates of 1.0 micrograms of DNA per milligram of gold or higher, precipitation should be apparent immediately after calcium chloride is added.

After precipitation, the tube is centrifuged briefly (10–15 seconds) to pellet the coated gold particles. The supernatant is removed and discarded and the pellet is washed several times with ethanol until virtually all of the water has been removed from the coated particle preparation. Between each ethanol wash, the preparation is spun and the supernatant discarded. The coated particles of the final pellet, containing known amounts of both DNA and gold, are resuspended in an evaporable liquid, preferably 100% ethanol, optionally containing an appropriate amount of an additive that provides a slight temporary adhesive effect desired for joining the coated particles to the sample cartridge. A suitable adhesive is polyvinyl pyrrolidone (PVP). The amount of adhesive required in the evaporable liquid depends upon the gas pressure to which the sample cartridges will be exposed during subsequent particle acceleration and also upon the type of tubing used. For gas pressures in the range of 100 to 150 psi, no adhesive is required. Between 150 and 300 psi, PVP at 0.1 milligram per milliliter is appropriate. PVP at 0.2 milligrams per milliliter is suitable at pressures between 300 and 500 psi. At pressures of 500–800 psi, 0.3 milligrams per milliliter of PVP is a suitable amount.

Some care should be taken in determining the total volume in which to resuspend the coated particles. The volume depends upon the desired amount of biological substance per delivery, the actual DNA loading rate, the desired particle density in the final sample cartridge, and the internal volume per length of tubing. One of ordinary skill will also recognize that the preferred amount of DNA per delivery and particles per delivery will vary with the nature of the target, the density at which the particles are coated, and the desired outcome of the transfer (e.g. transient expression or stable integration). Therefore, each of the stated variables, including the concentration at which the particles are loaded into the tubing, should be experimentally optimized.

After settling upon a desired particle loading rate, desired particle density and the volume capacity per unit length of tubing, one can readily determine the total volume of the evaporable liquid in which to resuspend the coated particles. A suitable sample cartridge length has been found to be about a ½ inch length of a tubing having in internal capacity of between about 0.6 and 1 milliliter per 7 inch length. In tubing having 1 ml/7" capacity, simple calculation demonstrates that if 0.5 milligrams of gold are desired in a ½ inch sample cartridge, the particles are prepared at a concentration of 7 milligrams of gold per milliliter. Likewise, for a 0.25 milligram sample in a ½ inch cartridge, a 3.5 milligram per milliliter concentration is appropriate. Concentrations that achieve other particle densities are calculated in the same way.

To achieve complete transfer of the coated particles into the evaporable liquid, it is recommended that the pellet be transferred to the storage tube in several partial transfer steps. For example, the coated particles can be resuspended in a small volume (500 microliters) of the liquid with optional adhesive, vortexed, briefly sonicated (2–3 seconds) and transferred to a clean tube. It is recommended that the tube be formed of a material to which the biological substances do not stick, such as polypropylene culture tube. These small volume transfers can be repeated until all the coated particles have been transferred to the tube. If desired, the tubes containing suspended coated particles can be sealed with Parafilm and stored for several months at −20° C. When the coated particles have been completely transferred, preparation of the sample cartridges can begin. If the tubes have been stored, they should be warmed to room temperature before unsealing for use in the particle-depositing method.

Before the tubing is cut into suitable lengths as described above, it is necessary to remove any end portions of the tubing in which particle distribution is uneven. The distribution of particles in the tubing can be tested operationally in the gas driven particle acceleration apparatus as follows under actual delivery conditions. The following test conditions are suitable, although other tests for determining and comparing the particle delivery profile of prepared sample cartridges can readily be devised.

Test cartridges of desired length are removed from opposite ends of the tubing. The particles from each tested cartridge are released from the concave inner surface under the pressure of 400 psi of gas and are directed into minimal water (3%) agar in 60 millimeter petri dishes without surface condensation. From each plate, a slice approximately 0.5 centimeters long is cut through the center of the target and mounted onto a microscope slide. It is important to test slices of comparable thickness when samples are compared. The slices are analyzed for particle depth and particle number under a microscope. The particles can be readily observed using a microscope with 10 X eyepiece equipped with a micrometer. At the top surface of the agar the particles are most dense, with density decreasing with increasing depth into the agar slice. Areas of high, medium, and low particle density are noted in each slice. The eyepiece micrometer is aligned to zero at a depth approximately equal to the deepest penetration of the particles. The micrometer value at the agar surface is the particle depth. Typical particle depths after delivery into minimal water agar at 400 psi are about 100–120 micrometers when 0.95 micron amorphous gold particles are used and about 260–300 micrometers for 1–3 micron gold spherical particles or beads.

If particle depth and density are similar, then cartridges derived from tubing section between the ends are acceptable for use. However, should the two ends differ markedly from each other or the standard, additional pairs of opposite end samples should be tested until both ends yield comparable results. When comparable results are obtained from both ends, the remaining length of tubing is cut into pieces of suitable length using a scalpel and a ruler. The sample cartridges thus prepared can be stored at 4° C. with desiccant in a Parafilm-sealed and labelled vial for up to two months at 4° C.

Loading of the tubing is aided considerably by an apparatus that can accommodate the filled tubing in a generally horizontal orientation, can rotate the tubing to distribute the particles and can facilitate introduction of the liquid-drying gas into the coated tubing. In accordance with the present method, a suitable apparatus 10 that facilitates deposition of coated particles from a suspension onto the inner concave surface of a length of tubing containing the suspended particles, is depicted in FIGS. 1–5.

The apparatus includes a tubing roller 12 rotatably mounted to a base 14 in a generally horizontal orientation. The base 14 can be of any size and shape, and should be at least as long as the particle-filled tubing that is intended to be coated. The base 14 can include leveling means and a spirit level to facilitate the horizontal positioning of the tubing roller. Two or more mounts 16, 18 attached to, or formed as part of, the base 14 rotatably engage the tubing roller 12, and direct proper rotation about the axis of rotation with minimal friction and precession. The mounts 16, 18 and the tubing roller 12 are preferably rotatably engaged with each other at or near the ends of the tubing roller 12. Holes passing through the mounts 16, 18 are sized and shaped to accommodate the ends of the tubing roller 12. Inner surfaces of the holes that contact the tubing roller 12 are preferably formed of a low friction material. For identification purposes only, a first mount is the mount closest to the first end of the tubing bore, while a second mount is the mount closest to the second end of the tubing bore.

The tubing roller 12 can be formed of any solid, durable material such as wood, plastic, metal or the like. A preferred configuration of the tubing roller 12 is generally cylindrical. The tubing roller 12 has sufficient length along the axis of rotation to receive and secure substantially the entire length of tubing. The other dimensions of the tubing roller 12 are not critical.

The tubing roller 12, shown in cross-section in FIG. 3, includes an axis of rotation and a tubing bore 20 coaxial with the axis of rotation. The tubing bore 20 is positioned so that a length of tubing received therein shares the same axis of rotation as the tubing roller 12. The tubing bore 20 extends into the tubing roller 12 from an opening 22 at a first end of the tubing bore. The tubing bore 20 is sized in length, width and depth to accommodate the tubing and is preferably generally cylindrical. The opening 22 is adapted to receive the length of tubing into the tubing bore 20. To facilitate insertion of the tubing into the tubing bore 20, the opening 22 at the first end of the tubing bore is wider than the bore 20 itself and preferably flares outward from the bore 20.

A second end of the tubing bore 20 is within the tubing roller 12. Thus, the tubing bore 20 does not pass linearly from one end of the tubing roller 12 completely through to the other end. The second end of the bore 20 is, however, in fluid communication with gas delivery means, as described below, for uninterrupted delivery of a liquid-drying gas from an external source at a suitably controlled flow rate into the second end of the bore 20, through the bore 20 and out the opening 22.

It is desirable that tubing within the tubing roller 12 be visually observable during use. Accordingly, a portion of the tubing roller 12 can be removed and replaced with a window 24 formed of a glass or plastic material, such as polycarbonate, that permits visual access to the received tubing, as is best shown in FIGS. 1, 3 and 4. The window 24 is most preferably transparent. For maximum tubing stability and visibility, the window 24 is preferably positioned so as to constitute one surface of the tubing bore 20, as is shown in FIG. 3. The window 24 can be held in place using any suitable adhesive 26 that sticks to both the window material and the tubing roller 12, such as a silicone adhesive. Although it is preferred that the window extend along most of the length of the tubing bore 20 through the tubing roller 12, one or more smaller windows, offering reduced visibility of the tubing would also be acceptable. If the window extends the length of the tubing bore 20, as shown in the embodiment illustrated here, the window can also serve as the fluid seal to permit the drying gas to be contained in the bore 20.

As an alternative configuration, the bore 20 in the roller 12 could be made to restrain the tubing in place without the window 24. This could be done by imbedding the bore 20 in the roller 12 so that the bore extends more than 1800 around the tubing to retain the tubing in place. A smaller opening to the top of the roller 12 could be provided to provide visual access. If this alterative is used, it may be necessary to seal the exterior of the tubing to the interior of the bore 20 in the fitting 42, to prevent excess leakage of drying gas.

The tubing roller 12 can also be provided with endpieces and mounting fittings, for example, shafts, blocks or plates, that are also formed of a durable, low friction material and compatible in size and shape with mounting holes provided on the mounts 16, 18. If securely attached to the rotatable tubing roller, the mounting endpieces and fittings must also be rotatable in the mount holes, and would, therefore, preferably be cylindrical. If the tubing roller includes an endpiece or fitting at the end that receives the tubing, the tubing bore 20 must also pass therethrough so as not to impede entry of the tubing. Likewise, the second end of the tubing bore 20 and associated portions of the gas delivery means can be located in a fitting rather than in the tubing roller per se. Such is the case in the exemplified embodiment. Bushings 28 can be included between the mounts 16, 18 and the tubing roller 12 (or its fittings) to reduce rotational friction.

In the exemplified embodiment, portions of the gas delivery means are incorporated directly into the mount 18. Cutaway views of the mount 18 are shown in FIGS. 2 and 5. The preferred gas delivery means includes in the gas flow path a controllable valve 30 for regulating gas flow rate and a gas flow meter 32 (available commercially from Dwyer) for monitoring the flow rate of gas through the gas delivery means and into the second end of the bore 20. Alternatively, gas flow rate can be regulated and monitored externally at the gas source. In the exemplified embodiment, a first gas conduit 34, adapted for connection to a source of liquid-drying gas, passes across and through the interior of the mount 18 to an inlet of the flow meter 32 under control of the controllable valve 30. An outlet from the flow meter 32 connects to a second gas conduit 36 that passes across and through the mount 18 to the exterior. A third gas conduit 38 passes from the exterior back into the mount 18. A length of tubing 40 external to the mount 18 joins the second 36 and third 38 gas conduits, bringing them into fluid communication with each other and bringing the source of the gas into fluid communication with the tubing bore 20, as follows. As is best shown in FIGS. 2 and 5, a cylindrical fitting 42, attached to the tubing roller 12, is rotatably engaged in the hole of the mount 18 and includes a V-shaped annular channel 44 about its circumference. The third gas conduit 38 opens onto the V-shaped channel 44, bringing the two into fluid communication. At least one additional bore 46 through the cylindrical fitting connects the bottom of the V-shaped channel 44 to the tubing bore 20, thereby ensuring uninterrupted fluid communication between the source of the liquid-drying gas and the tubing bore 20. Thus, fluid communication is maintained along the entire length of the described gas delivery means. The fitting 42 with its V-shaped annular channel 44 and bore 46 may properly be considered to be part of the gas delivery means of the described apparatus, even though it is physically attached to the tubing roller 12. One of ordinary skill will also appreciate the potential use of additional or other gas tubing, gas conduits and the like to ensure fluid communication between a source of gas and the tubing bore 20.

The tubing roller 12 is also operably connected to a rotator 48 that directs rotation of the tubing roller 12 about the axis of rotation. The rotator 48 can be powered in any way (for example, electrical or mechanical energy powering direct or indirect rotation of the tubing roller 12, but must provide sufficient power to rotate the tubing roller 12 about the axis of rotation at a constant rate of between 10 and 30 revolutions per minute (rpm) for at least 30 seconds. The rotator 48 can be connected to any portion of the tubing roller 12, as long as axial rotation is not constrained. The rotator 48 preferably attaches directly to a shaft 50 which is itself attached at the end of the fitting 42 on the tubing roller 12 that engages mount 18. A suitable rotator 48 that can attach directly to the shaft 50 is an electrically actuated gear motor, such as a Barnant Mixer Series 20 motor, which can be remotely controlled using an associated variable speed power supply 52. The rotator 48 need not be attached to the base 14 but is preferably attached thereto for increased stability.

In use, the sample tubing is filled with the coated-particle uniform suspension, using an aspirator as described above in connection with the present method, and the filled tubing is inserted into the flared end of the tubing bore 20. The tubing is advanced into the bore 20 until fully inserted. During insertion of the tubing, the aspirator remains attached. When the beads have settled, as described, the aspirator is detached from the tubing and the evaporable liquid is drawn off at a constant rate of about 2–3 inches of liquid per second, preferably using a constant flow rate peristaltic pump (labelled in FIG. 1 as P). The rotator 48 is then engaged to rotate the tubing roller 12 around the axis of rotation at a rate that allows the settled particles to smear and coat at least a portion of the inner concave surface of the tubing. A rate of 20 rpm for a period of 30 seconds is sufficient. After smearing, the liquid-drying gas is allowed to enter through the gas conduits 34, 36, 38 and into the tubing in the tubing bore at a flow rate of 350–400 milliliters per minute until the particles in the tubing are dry.

The present invention is not intended to be limited to the embodiments disclosed herein, but to encompass all such variations and modifications that come within the scope of the following claims.

We claim:

1. A method for depositing particles within a length of tubing, said method comprising the steps of:

preparing a suspension of particles in an evaporable liquid medium;

introducing the suspension into a length of tubing having a concave inner surfaces, a first ends, and a second end;

placing the tubing into a generally horizontal orientation, thereby allowing particles from the suspension to settle onto a portion of the inner surface of the tubing;

removing most of the evaporable liquid from the tubing after the particles have been allowed to settle;

rotating the tubing about a generally horizontal axis of rotation for a time sufficient to distribute the settled particles over the inner surface of the tubing; and drying the distributed particles.

2. The method of claim 1, wherein the introducing step comprises:

coupling a syringe to the first end of the tubing;

placing the second end of the tubing into the suspension; and aspirating the syringe to draw the suspension into the tubing.

3. The method of claim 1, wherein the removing step comprises:

withdrawing the evaporable liquid from the tubing with a pump connected to one end of the tubing, wherein the liquid is withdrawn through the pump at a rate sufficiently low to avoid removing the settled particles.

4. The method of claim 1, wherein the drying step comprises:

passing a liquid-drying gas over the inner surface of the rotated tubing for a period of time sufficient to dry the particles.

* * * * *